US011045447B2

(12) United States Patent
Alkon

(10) Patent No.: US 11,045,447 B2
(45) Date of Patent: Jun. 29, 2021

(54) METHODS FOR INDUCING SYNAPTOGENESIS WITH SYNAPTIC GROWTH FACTOR ACTIVATING COMPOUNDS

(71) Applicant: NEUROTROPE BIOSCIENCE, INC., New York, NY (US)

(72) Inventor: Daniel L. Alkon, Chevy Chase, MD (US)

(73) Assignee: Synaptogenix, Inc., New York, NY (US)

(*) Notice: Subject to any disclaimer, the term of this patent is extended or adjusted under 35 U.S.C. 154(b) by 0 days.

(21) Appl. No.: 16/914,399

(22) Filed: Jun. 28, 2020

(65) Prior Publication Data
US 2020/0323817 A1 Oct. 15, 2020

Related U.S. Application Data

(63) Continuation of application No. PCT/US2019/032762, filed on May 17, 2019.

(60) Provisional application No. 62/673,590, filed on May 18, 2018.

(51) Int. Cl.
| | | |
|---|---|---|
| *A61K 31/365* | (2006.01) | |
| *A61P 25/28* | (2006.01) | |
| *A61K 9/00* | (2006.01) | |
| *C07K 14/49* | (2006.01) | |
| *A61K 38/00* | (2006.01) | |

(52) U.S. Cl.
CPC .......... *A61K 31/365* (2013.01); *A61K 9/0019* (2013.01); *A61P 25/28* (2018.01); *C07K 14/49* (2013.01); *A61K 38/00* (2013.01)

(58) Field of Classification Search
CPC .... A61K 31/365; A61K 9/0019; A61K 38/00; A61P 25/28; C07K 14/49
See application file for complete search history.

(56) References Cited

U.S. PATENT DOCUMENTS

| | | | | |
|---|---|---|---|---|
| 6,825,229 B2 * | 11/2004 | Etcheberrigaray | ........ | A61P 3/02 514/451 |
| 7,977,377 B2 * | 7/2011 | Sun | ......... | A61P 25/18 514/455 |
| 8,703,812 B2 * | 4/2014 | Alkon | ...... | A61P 25/00 514/450 |
| 9,050,299 B2 * | 6/2015 | Bankiewicz | ............ | A61P 25/00 |
| 9,107,890 B2 * | 8/2015 | Alkon | .......... | A61K 9/0019 |
| 9,119,825 B2 * | 9/2015 | Nelson | .................. | A61K 31/201 |
| 9,163,032 B2 * | 10/2015 | Alkon | ........ | C07J 1/007 |
| 9,539,235 B2 * | 1/2017 | Etcheberrigaray | .... | A61K 31/00 |
| 9,597,312 B2 * | 3/2017 | Sun | ......... | A61P 25/00 |
| 9,889,183 B2 * | 2/2018 | Alkon | ...... | A61P 43/00 |
| 9,974,832 B2 * | 5/2018 | Zohar | ........ | A61K 38/1825 |
| 10,323,011 B2 * | 6/2019 | Nelson | ........ | C07D 303/42 |
| 10,696,644 B2 * | 6/2020 | Nelson | ........ | C07D 303/42 |
| 2003/0171356 A1 | 9/2003 | Etcheberrigaray et al. | | |
| 2008/0004332 A1 | 1/2008 | Alkon | | |
| 2008/0234197 A1 * | 9/2008 | Allam | .................. | A61K 47/543 |
| 2014/0315990 A1 * | 10/2014 | Alkon | ........ | A61P 9/00 514/450 |

FOREIGN PATENT DOCUMENTS

| | | | |
|---|---|---|---|
| WO | 2004/004641 A2 | 1/2004 | |
| WO | 2006/031337 A2 | 3/2006 | |
| WO | 2009/099563 A2 | 8/2009 | |

OTHER PUBLICATIONS

Duman et al. Synaptic Dysfunction in Depression: Potential Therapeutic Targets. Science. Oct. 5, 2012; 338(6103): 68-72.*
Alkon D. et al, "Evidence of Sustained Low Dose Bryostatin Efficacy for Treatment of Alzheimer's Disease: Consistency of Multiple Evaluation Analyses", Journal of Prevention of Alzheimer's Disease Oct. 1, 2018 Springer NLD, 5 (1) (Oct. 1, 2018), Abstract.
Etcheberrigaray R. et al, "Therapeutic Effects of PKC Activators in Alzheimer's Disease Transgenic Mice", PNAS 101(30):11141-11146 (Jul. 27, 2004).
Farlow M.R. et al., "Bryostatin-1 Improves Cognition and Daily Living Tasks in Moderate to Severe Alzheimer's Disease: Preliminary Report of a Phase 2 Study", Alzheimer's & Dementia: The Journal of the Alzheimer's Association 13(7):p. 1476 (Jul. 19, 2017).
Greb E., "Bryostatin is Safe in Patients With Moderate to Severe Alzheimer's Disease" Neurology Reviews 25(11):28 (Nov. 2017), retrieved from the Internet: URL:https://www.mdedge.com/neurology/article/150497/alzheimers-cognition/bryostatin-safe-patients-moderate-severe-alzheimers [retrieved on Jul. 22, 2019].
Nelson T.J. et al., "Bryostatin Effects on Cognitive Function and PkCε in Alzheimer's Disease Phase IIa and Expanded Access Trials", Journal of Alzheimer's Disease 58(2):521-535 (2017).
Schrott L.M. et al., "Acute Oral Bryostatin-1 Administration Improves Learning Deficits in the APP/PS1 Transgenic Mouse Model of Alzheimer's Disease", Current Alzheimer Research 12(1):22-31 (Jan. 1, 2015).
Thompson R. et al, "Significant Cognitive Improvement With Bryostatin for Advanced Alzheimer's Patients in the Absence of Memantine", Alzheimer's and Dementia Jul. 1, 2018 Elsevier Inc. NLD 14(7):Supplement (Jul. 1, 2018), Abstract.
Anonymous: "A Study Assessing Bryostatin in the Treatment of Moderately Severe to Severe Alzheimer's Disease", ClinicalTrials.gov (Aug. 12, 2017), retrieved from the Internet: URL:https://web.archive.org/web/20170812140447/ https://clinicaltrials.gov/ct2/show/NCT02431468 [retrieved Jul. 22, 2019).
Anonymous: "An Alzheimer's Candidate Has Garnered Optimism in Clinical Trials", Genetic Engineering & Biotechnology News (Apr. 1, 2018), retrieved from the Internet: URL:https://www.genengnews.com/magazine/312/the-scoop-alzheimers-drug-tries-to-build-up-a-head-of-steam/ [retrieved on Jul. 22, 2019).

(Continued)

*Primary Examiner* — Gregory S Emch
(74) *Attorney, Agent, or Firm* — Scully, Scott, Murphy & Presser, P.C.

(57) ABSTRACT

A method for treating Alzheimer's disease (AD) by administering to an AD patient a PKC activator, such as a bryostatin-1, without administering a NMDA receptor antagonist, such as memantine.

18 Claims, 8 Drawing Sheets
(8 of 8 Drawing Sheet(s) Filed in Color)

(56) References Cited

OTHER PUBLICATIONS

Anonymous: "Bryostatin-1 Effective for Alzheimer's Disease", Healio Psychiatric Annals (May 2, 2017), retrieved from the Internet: URL:https://web.archive.org/web/20171120031746/https://www.healio.com/psychiatry/alzheimers-disease-dementia/news/online/%7Bd4815fc2-7b17-4ef0-947e-b01fele1bff9%7D/bryostatin-1-effective-for-alzheimers-disease [retrieved on Jul. 22, 2019).
International Search Report dated Aug. 5, 2019 received in International Application No. PCT/US2019/032762.
Sen, A., et al., "Loss in PKC Epsilon Causes Downregulation of MnSOD and BDNF Expression in Neurons of Alzheimer's Disease Hippocampus", Journal of Alzheimer's Disease (2018), Accepted Mar. 19, 2018, pp. 1173-1189, 63.

* cited by examiner

METHODS FOR INDUCING SYNAPTOGENESIS WITH SYNAPTIC GROWTH FACTOR ACTIVATING COMPOUNDS

CROSS-REFERENCE TO RELATED APPLICATIONS

This application is a continuation of PCT/US2019/032762, filed May 17, 2019 and claims priority from U.S. Provisional Application No. 62/673,590, filed May 18, 2018, which is herein incorporated by reference in its entirety.

BACKGROUND

All references cited herein are expressly incorporated by reference.

Treatments of Alzheimer's disease (AD) have been based on immunotherapy for pathologic hallmarks of the autopsy AD brain, amyloid plaques and neurofibrillary tangles generated by hyperphosphorylated tau protein. Other therapeutic strategies have focused on enhancement or blockade of neurotransmitters at synaptic junctions (Reisberg et al. *N Engl J Med.* 2003 Apr. 3; 348(14):1333-41). While the latter have generated drugs with some symptomatic efficacy, the approved drugs have thus far not been effective in preventing, improving, and/or reversing the progressive neurodegeneration that ultimately causes major cognitive dysfunction and functional decline in AD patients (Farlow et al., *Clin. Ther.* 2010 July; 32(7):1234-51. doi: 10.1016; Farlow et al., *BMC Neurology* 2011 vol. II, article 57; and Farlow, *Neurology* 2005 65:S1-S4). This lack of efficacy is likely related to the lack of close correlation demonstrated by plaques and tangles with the degree of cognitive deficits.

On the other hand, cognitive deficits have been shown to correlate closely with the loss of synapses as measured directly or indirectly at autopsy (Terry et al., *Ann Neurol.* 1991 October; 30(4):572-80). An effective therapeutic for AD should be directed toward, not only the causes, but also the consequences of the characteristic progressive neurodegeneration. Based on the synaptic loss in AD, there would be a significant benefit in a therapeutic strategy that can restore lost synapses in AD brains.

SUMMARY

Methods of treating Alzheimer's disease (AD) are described herein including administering to an AD patient in need thereof a protein kinase C (PKC) activator, wherein the patient is not administered an NMDA receptor antagonist. In embodiments, the PKC activator is bryostatin or analog thereof. In embodiments, the PKC activator is bryostatin-1.

Methods of treating Alzheimer's disease are also described herein including administering to an AD patient in need thereof a PKC activator, wherein the treatment excludes administration of a NMDA receptor antagonist. In embodiments, the PKC activator is bryostatin or analog thereof. In embodiments, the PKC activator is bryostatin-1.

Methods of treating Alzheimer's disease are also described herein including administering to an AD patient in need thereof bryostatin-1 wherein the patient is not also administered memantine.

Methods of treating Alzheimer's disease are also described herein including administering to an AD patient in need thereof no more than or less than about 30, 35, or 40 mcg (or range therein) of bryostatin-1 wherein the patient is not also administered memantine. In embodiments, the patient is administered less than 40 mcg bryostatin-1. In some embodiments the patient is administered about 20 mcg bryostatin-1.

Methods of treating Alzheimer's disease are also described herein including administering to an AD patient in need thereof about 20 mcg or 25 mcg (or range therein) of bryostatin-1 wherein the treatment excludes memantine.

Methods of treating Alzheimer's disease are also described herein including administering to an AD patient in need thereof no more than or less than about 30, 35, or 40 mcg (or range therein) of bryostatin-1 wherein the patient is not receiving memantine treatment. In some embodiments the patient is administered 15-40 mcg bryostatin-1. In other embodiments, the patient is administered less than 40 mcg bryostatin-1

Methods of treating Alzheimer's disease are also described herein including administering to an AD patient in need thereof about 20 mcg or 25 mcg (or range therein) of bryostatin-1 wherein the patient is not receiving memantine treatment. In some embodiments the patient is administered about 20 mcg bryostatin-1.

Methods of treating Alzheimer's disease are also described herein including administering to an AD patient in need thereof about 15 mcg to about 25 mcg (or range therein) of bryostatin-1 wherein the treatment excludes memantine and provides cognitive improvement. In some embodiments the patient is administered about 20 mcg bryostatin-1.

Methods of treating Alzheimer's disease are also described herein including administering to a patient in need thereof about 20 mcg or 25 mcg (or range therein) of bryostatin-1 wherein the treatment excludes memantine and is provided for at least or more than 4, 5, or 6 weeks.

Each of the methods described herein may further include the administration of a compound selected from the group consisting of galantamine, donepezil, rivastigimine, physostigmine, tacrine, huperzine A, ladostigil, and combinations thereof.

In some embodiments, the patient in need of treatment is a patient diagnosed with mild Alzheimer's disease. In other embodiments, the patient is diagnosed with mild to moderate Alzheimer's disease.

In some embodiments, the patient in need of treatment is a patient diagnosed with moderate Alzheimer's disease. In other embodiments, the patient is diagnosed with moderate to severe Alzheimer's disease. In other embodiments, the patient in need of treatment is a patient diagnosed with severe Alzheimer's disease.

In some embodiments, the patient is diagnosed with early onset Alzheimer's disease. In other embodiments, the patient is diagnosed with late onset Alzheimer's disease.

Compositions for treating Alzheimer's Disease are also described herein and include at least one PKC activator, the composition being free of any NMDA receptor antagonist. In some embodiments, the PKC activator is bryostatin or an analogue thereof. In particular embodiments, the PKC activator is bryostatin-1. In embodiments, the compositions are free of memantine.

BRIEF DESCRIPTION OF THE DRAWINGS

The patent or application contains at least one drawing executed in color. Copies of this patent or patent application publication with color drawing(s) will be provided by the Patent and Trademark Office upon request and payment of the necessary fee.

Some specific embodiments of the disclosure may be understood by referring, in part, to the following description and the accompanying drawings.

DETAILED DESCRIPTION

Figure 1:
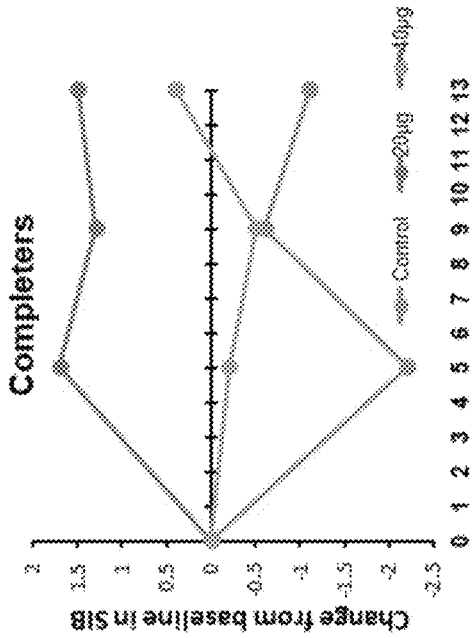
FIG. 1 includes graphs showing the SIB change from baseline compared to placebo for the modified intent-to-treat (mITT) population and also the Completers population treated with Bryostatin.
Figure 1:
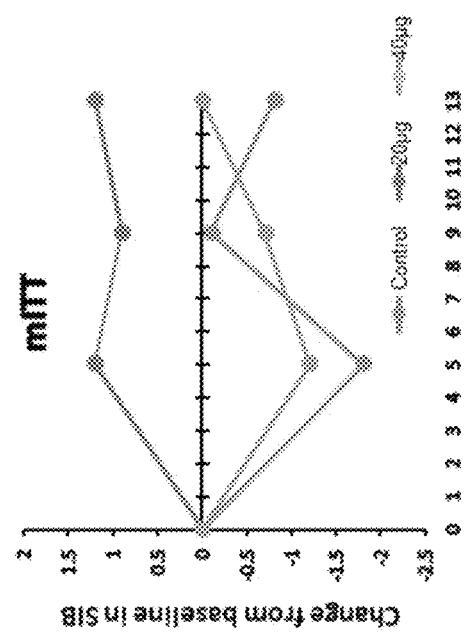

In general, the present disclosure provides methods for treating Alzheimer's disease using PKC activators in the absence of any NMDA receptor antagonist, such as memantine. As used herein, the term "protein kinase C activator" (i.e., "PKC activator") refers to a substance that increases the rate of the reaction catalyzed by protein kinase C, upregulates the expression of PKC (e.g., upregulates the expression of PKCα, PKC βII, PKC γ and/or PKC ε), or otherwise facilitates the activation of PKC. In certain embodiments, the PKC activator may be any of bryostatins 1-20, a bryolog, neristatin, a polyunsaturated fatty acid, or a combination of two or more of any of the foregoing substances.

As used herein, the term "NMDA receptor antagonist" refers to a substance that antagonizes (i.e., inhibits) the action of NMDA receptors. Some examples of NMDA receptor antagonists include memantine, drug combinations containing memantine, dextromethorphan, ketamine, phencyclidine (PCP), methoxetamine (MXE), and nitrous oxide ($N_2O$). Any one or all of the foregoing NMDA receptor antagonists may be excluded from the method of treating AD.

In certain embodiments, the present disclosure provides methods comprising administering to a human subject with Alzheimer's disease a pharmaceutically effective amount of a PKC activator without administering any NMDA receptor antagonist, such as memantine. The PKC activator may be administered as part of a composition suitable for administration to a human subject. The compositions used in the methods of the present disclosure may be administered via any suitable route, such as, for example, orally, intraperitoneally, subcutaneously, intranasally, buccally, trans-dermally intramuscularly, intrarectally, intravenously, or by oral inhalation.

In some embodiments, the present disclosure provides methods comprising administering to a human subject with Alzheimer's disease a composition consisting essentially of, or containing exclusively, a pharmaceutically effective amount of a PKC activator in a pharmaceutically suitable carrier, optionally along with one or more pharmaceutically inactive auxiliary agents. Thus, the composition preferably does not include a second active agent, particularly a NMDA receptor antagonist. Compositions and methods consisting essentially of a PKC activator exclude additional active compounds, such as memantine.

Bryostatins, in particular, may be used as a PKC activator in the methods of the present disclosure. The term "bryostatins" is herein meant to also include the numerous known analogues thereof, unless otherwise specified. The bryostatins are a family of naturally occurring macrocyclic compounds originally isolated from marine bryozoa. Currently, there are about 20 known natural bryostatins which share three six-membered rings designated A, B and C, and which differ mainly in the nature of their substituents at C7 ($OR^A$) and C20 ($R^B$). A representative generic structure of the bryostatins is provided below:

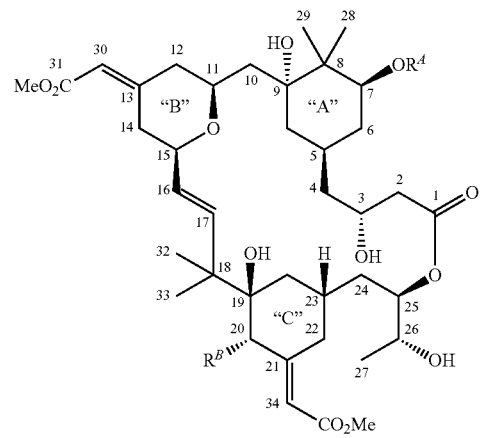

Bryostatin 1 and analogues (derivatives) of bryostatin 1 are described in U.S. Pat. No. 4,560,774, the contents of which are herein incorporated by reference in their entirety. Some examples of bryostatins that may be used as a PKC activator in methods of the present disclosure include bryostatin 1, bryostatin 2, bryostatin 3, bryostatin 4, bryostatin 5, bryostatin 6, bryostatin 7, bryostatin 8, bryostatin 9, bryostatin 10, bryostatin 11, bryostatin 12, bryostatin 13, bryostatin 14, bryostatin 15, bryostatin 16, bryostatin 17, bryostatin 18, bryostatin 19, and bryostatin 20.

Analogues of bryostatins, commonly referred to as bryologs, may or may not be used in the methods of the present disclosure. Bryologs are structural analogues of bryostatin. While bryostatin has two pyran rings and one 6-membered cyclic acetal, in most bryologs one of the pyrans of bryostatin is replaced with a second 6-membered acetal ring. This modification reduces the stability of bryologs, relative to bryostatin, for example, in both strong acid or base, but has little significance at physiological pH. Bryologs also have a lower molecular weight (ranging from about 600 to 755), as compared to bryostatin (988), a property which may facilitate transport across the blood-brain barrier. Examples of suitable bryologs include, but are not limited to analogs and derivatives of bryostatins, such as those described in U.S. Pat. Nos. 6,624,189, 7,256,286 and 8,497,385, the disclosures of which are incorporated herein by reference in their entirety.

Another example of suitable PKC activators include potassium channel activators, such as, for example, diazoxide. In certain embodiments, neristatins, such as neristatin 1, may be used in the methods of the present disclosure for treating Alzheimer's disease. Other suitable PKC activators include, but are not limited to, phorbol-2-myristate-13-acetate (PMA), okadaic acid, 1α,25-dihydroxyvitamin D3, 12-deoxyphorbol-13-acetate (prostratin), 1,2-dioctanoyl-sn-glycerol (DOG), 1-oleoyl-2-acetyl-sn-glycerol (OAG), (2S, 5S)-(E,E)-8-(5-(4-(trifluoromethyl)phenyl)-2,4-pentadienoylamino)benzolactam (α-amyloid precursor protein modulator), cis-9-octadecenoic acid (oleic acid), ingenol 3-angelate, resiniferatoxin, L-α-Phosphatidyl-D-myo-inositol-4,5-bisphosphate, triammonium salt (PIP2), phorbol-12,13-dibutyrate, 8(S-hydroxy-(5Z,9E,11Z,14Z)-eicosatetra-enoic acid (8(S)-HETE), 12β-[(E,E)-5-Phenyl-2,4-pentadienoyloxy]daphnetoxin (merzerein), clomiphene citrate, sodium oleate, phorbol 12,13-diacetate, phorbol-12,13-didecanoate, 1,2-dipalmitoyl-sn-glycerol, 1-Stearoyl-2-linoleoyl-sn-glycerol, phorbol-12,13-didecanoate, 1,2-dipalmitoyl-sn-glycerol, 1-stearoyl-2-linoleoyl-sn-glycerol, phorbol 12,13-dihexanoate, prostratin and its analogs, resiniferonol 9,13,14-ortho-phenylacetate, C-8 ceramide, 1,6-bis(Cyclohexyloximinocarbonylamino)hexane; 1,6-Di(O-(carbamoyl)cyclohexanone oxime)hexane (RHC-80267), (+/−)-1-oleoyl-2-acetylglycerol, 5(S),6(R),15(S)-TriHETE (Lipoxin A4), (−)-Indolactam V, SC-9, SC-10, zoledronic acid monohydrate, 12-deoxyphorbo 13-angelate 20-acetate, 6-(N-decylamino)-4-hydroxymethylindole, 4α-phorbol 12,13-dibutyrate, 1,2-dihexanoyl-sn-glycerol, zoledronic acid disodium salt tetrahydrate, arachidonic acid methyl ester, arachidonic acid-d8. In some embodiments, any of the above bryologs, potassium channel activators, or neristatins may be excluded from the method. Alternatively, in some embodiments, any of the above bryologs, potassium channel activators, or neristatins may be used in combination with one or more bryostatins in the method described above.

As used herein, "a pharmaceutically effective amount" is an amount of a pharmaceutical compound or composition having a therapeutically relevant effect on Alzheimer's disease. A therapeutically relevant effect typically relates to or is evidenced by at least some improvement in a biomechanical process (e.g., gait, use of limbs, and the like) or a change in the cellular, physiological or biochemical parameters associated with any of the causes of Alzheimer's disease. A therapeutically relevant effect may also be evident in an improved cognitive ability, such as short-term memory or problem solving.

The PKC activator is typically within a pharmaceutically acceptable carrier (i.e., diluent) when administered. As used herein, and as generally understood in the pharmaceutical arts, the term "pharmaceutically acceptable" generally refers to those compounds, materials, compositions, and/or dosage forms that are, within the scope of sound medical judgment, suitable for entering a living organism or living biological tissue, preferably without significant toxicity, irritation, or allergic response. The pharmaceutical compositions of the present invention may be formulated for administration in liquid or solid form. In the pharmaceutical composition, the compound is generally dispersed in the physiologically acceptable carrier, by being dissolved or emulsified in a liquid carrier, or mixed (i.e., blended or compounded) with a solid carrier. The carrier should be compatible with other ingredients of the formulation and physiologically safe to the subject. Examples of suitable aqueous and non-aqueous carriers that may be employed in the pharmaceutical compositions of the invention include, for example, water, ethanol, polyols (such as glycerol, propylene glycol, polyethylene glycol, and the like), vegetable oils (such as olive oil), injectable organic esters (such as ethyl oleate), and suitable mixtures thereof. In different embodiments, the pharmaceutical formulation may be formulated for oral administration (e.g., as tablets, capsules, powders, granules, pastes, solutions, suspensions, drenches, or syrups); parenteral administration (e.g., by subcutaneous, intramuscular or intravenous injection as provided by, for example, a sterile solution or suspension); sublingual or buccal administration; transdermal administration; or nasal administration. The pharmaceutical composition may also include one or more pharmaceutically inactive auxiliary agents, such as pH buffering agents; sugars (e.g., lactose, glucose, sucrose, and oligosaccharides, such as sucrose, trehalose, lactose, or dextran); antimicrobials; and/or sweetening, flavoring, or coloring agents.

In certain embodiments, a pharmaceutically effective amount for bryostatins and/or bryologs may be from about 0.0000001 to about 5.00 mcg per kg host body weight per day, which can be administered in single or multiple doses. In some embodiments, the dosage level may be: from about 0.0000001 mcg/kg to about 2.50 mcg/kg per day; from about 0.0000005 mcg/kg to about 1.00 mcg/kg per day; from at least about 0.0000001 mcg/kg to about 2.50 mcg/kg per day; from at least about 0.00000005 mcg/kg to about 1.00 mcg/kg per day; from at least about 0.000001 mcg/kg to about 5.0 mcg/kg per day; or from about 0.00001 mcg/kg to about 5.0 mcg/kg per dose. In other embodiments, the dosage may be about 0.00000001 mcg/kg to about 0.00005 mcg/kg; 0.00005 mcg/kg to about 0.05 mcg/kg; about 0.0005 mcg/kg to about 5.0 mcg/kg per day; about 0.0001 mcg/kg to about 0.5 mcg/kg per dose; or 0.001 to 0.25 mcg/kg per dose.

In some embodiments, a pharmaceutically effective amount of a PKC activator may be an amount ranging from about 1 mcg to about 500 mcg per dose, or more particularly, from about 5 mcg to about 200 mcg per dose, or more particularly, from about 10 mcg to about 100 mcg per dose, or more particularly, from about 20 mcg to about 40 mcg per dose. In different embodiments, the PKC activator is administered in an amount of precisely or about 10, 15, 20, 25, 30, 35, 40, 45, or 50 mcg, or in an amount within a range bounded by any two of the foregoing values, wherein the term "about" generally indicates no more than ±10% or ±5% from a given value.

In some embodiments, the dosing is from about 1 μg/kg (3-25 μg/$m^2$) to 120 μg/kg (360-3000 μg/$m^2$). In other embodiments, the dosing is from about 0.04-0.3 μg/kg (1 μg/$m^2$) to about 1-10 μg/kg (25 μg/$m^2$). In other embodiments, the dosing is from about 0.01 μg/$m^2$ to about 25 μg/$m^2$. In other embodiments, the dosing is from about 0.0002-0.0004 μg/kg to about 0.05-1 μg/kg.

In some embodiments, the PKC activator is a bryostatin or analogue thereof and a pharmaceutically effective amount of the bryostatin or analogue thereof may be an amount ranging from about 1 mcg to about 500 mcg per dose, or more particularly, from about 5 mcg to about 200 mcg per dose, or more particularly, from about 10 mcg to about 100 mcg per dose, or more particularly, from about 20 mcg to about 40 mcg per dose. In some embodiments, the PKC activator is a bryostatin or analogue thereof administered at a dosage of about 0.001 to 100 mcg/kg; 0.01 to about 50 mcg/kg; about 0.1 to about 10 mcg/kg.

In some embodiments, the PKC activator is a bryostatin or bryolog, and the bryostatin or bryolog is used (administered) in an amount from about 0.0001 to about 1000 micrograms. In some embodiments, the bryostatin or bryolog is used in an amount of at least or about 0.0001, 0.0005, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, or 1000.0 micrograms, or an amount within a range bounded by any two of the foregoing values.

In some embodiments, the PKC activator present in the compositions used in the methods of the present disclosure is a bryostatin or bryolog, and the bryostatin or bryolog is used (administered) in an amount of less that 50 micrograms (i.e., 50 mcg, or 50 µg). In some embodiments, the bryostatin or bryolog is used in an amount of less than 45 mcg. In some embodiments, the bryostatin or bryolog is used in an amount of less than 40 mcg (40 µg). In other embodiments, the bryostatin or bryolog is used in an amount of less than 30 mcg (µg). In further embodiments to any of the foregoing embodiments, a lower limit of at least or above 1, 2, 3, 4, 5, 10, 15, 20, or 25 mcg may be used.

In some embodiments, the pharmaceutical composition will include bryostatin (e.g., bryostatin-1) in an amount of 0.1 mcg to 50 mcg, 0.1 mcg to 25 mcg, 0.1 mcg to 20 mcg, 0.1 mcg to 15 mcg, 0.5 mcg to 50 mcg, 0.5 mcg to 25 mcg, 0.5 mcg to 20 mcg, 0.5 to 15 mcg, 1 mcg to 50 mcg, 1 mcg to 25 mcg, 1 mcg to 20 mcg, 1 mcg to 15 mcg, 1.5 mcg to 50 mcg, 1.5 mcg to 25 mcg, 1.5 mcg to 20 mcg, 1.5 mcg to 15 mcg, 2 mcg to 50 mcg, 2 mcg to 25 mcg, 2 mcg to 20 mcg, 2 mcg to 15 mcg, 2.5 mcg to 30 mcg, 2.5 mcg to 25 mcg, 2.5 mcg to 20 mcg, 2.5 mcg to 15 mcg, 3 mcg to 25 mcg, 3 mcg to 20 mcg, or 3 mcg to 15 mcg, typically within a pharmaceutically acceptable carrier. Moreover, any of the foregoing amounts may also serve as a dosage, which may be administered, for example, once or twice per day, or by any other suitable regime as discussed above.

In some embodiments, the pharmaceutical composition include bryostatin (e.g., bryostatin-1) in an amount of 5 mcg to 20 mcg, 5 mcg to 10 mcg, 4 mcg to 6 mcg, 6 mcg to 8 mcg, 8 mcg to 10 mcg, 10 mcg to 12 mcg, 12 mcg to 14 mcg, 14 mcg to 16 mcg, 16 mcg to 18 mcg, or 18 mcg to 20 mcg. In some embodiments, the pharmaceutical compositions used in the methods include bryostatin (e.g., bryostatin-1) in an amount of 0.1 mcg, 0.25 mcg, 0.5 mcg, 1 mcg, 2.5 mcg, 3 mcg, 4 mcg, 5 mcg, 7 mcg, 7.5 mcg, 10 mcg, 12.5 mcg, 15 mcg, 17.5 mcg, or 20 mcg. Moreover, any of the foregoing amounts may also serve as a dosage, which may be administered, for example, once or twice per day, or by any other suitable regime as discussed above.

The pharmaceutical compositions used in the methods of the present disclosure may be administered by any suitable regimen, such as a regimen of 1 to 4 times per day. In some embodiments, the compositions are administered twice a week, once a week, once every two weeks, once every three weeks, once every four weeks, once every six weeks, once every eight weeks or less or more frequently depending on the needs of the patient. In some embodiments, the compositions used in the methods of the present disclosure may be administered as part of a course of treatment lasting for about 1 to about 30 days; about 1 to about 90 days; about 1 to about 120 days; about 1 to about 180 days; about 1 to 365 days; one year; two years; three years; or for the patient's lifetime. In some embodiments, the compositions used in the methods of the present disclosure may be administered as part of a course of treatment lasting for at least about 5 weeks; at least about 9 weeks; at least about 13 weeks; at least about 15 weeks. Nevertheless, the specific dose level and frequency of dosage for any particular host may be varied and will depend upon a variety of factors, including the activity of the specific compound employed, the metabolic stability and length of action of that compound, the age, body weight, general health, sex, diet, mode and time of administration, rate of excretion, drug combination, the nature of the disorder, the severity of the particular disorder, and the host undergoing therapy.

To facilitate a better understanding of the present invention, the following examples of specific embodiments are given. In no way should the following examples be read to limit or define the entire scope of this disclosure.

EXAMPLES

Example 1

In a double-blind, randomized, placebo-controlled trial, bryostatin was administered by intravenous infusion (~45 minutes) to patients with advanced Alzheimer's disease for 12 weeks at doses of 20 or 40 µg. Randomization was stratified at baseline by severe (MMSE-2, 4-9) and moderate (MMSE-2, 10-15) dementia, wherein MMSE-2 refers to Mini-Mental State Examination, version 2. The MMSE or Folstein test is a 30-point questionnaire that is used extensively in clinical and research settings to measure cognitive impairment. Low scores indicate greater impairment. Version 2 of the MMSE was published in 2010, expanding the original questionnaire's usefulness in populations with milder forms of cognitive impairment. Safety results were similar to placebo for 20 µg with more adverse events in the 40 µg group. The 20 µg dosing arm, but not the 40 µg dosing arm, showed sustained efficacy with respect to baseline as well as with respect to the Placebo group—as measured by positive changes in the Severe Impairment Battery (SIB). Importantly, this cognitive improvement persisted and increased 30 days after all bryostatin dosing had been completed. This improvement did not occur in the presence of memantine (NMDA receptor antagonist) background therapy.

Methods

Adults aged 55-85 with cognitive deficits present for at least 2 years, MMSE-2 of 4-15, inclusive, and a diagnosis of Alzheimer's dementia were randomly assigned to receive blinded intravenous infusions of bryostatin 24 µg or matching placebo at weeks 0 and 1. The 24 µg and 48 µg doses during the first two weeks of the 20 and 40 µg protocols respectively were considered to be "loading" doses thought to be beneficial from prior experience with Compassionate Use trial patients. Nelson et al., *Alzheimers Dis.* 2017 58: 521-535. In one arm, the two 24 µg doses were followed by 20 µg doses at weeks 5, 7, 9 and 11 with the Severe Impairment Battery (SIB) measured at baseline and weeks 5, 9, 13, and 15. In a second arm, the two 48 µg doses at weeks 0 and 1 were followed by 40 µg doses at weeks 5, 7, 9, and 11 with the SIB measured at baseline and weeks 5, 9, 13, and 15. The subjects were stratified by MMSE-2 in two strata: Stratum 1 (4-9) and Stratum 2 (10-15). The first primary endpoint was safety and tolerability, assessed by treatment emergent adverse events (TEAEs) with a sample size of 150 subjects randomized 1:1:1. Although efficacy was the secondary measure, the primary efficacy endpoint was SIB improvement at week 13 evaluated using a mixed model for repeated measures. A secondary efficacy endpoint was ADCS-ADL Sev. The primary safety population included all subjects who received at least 1 dose of study drug, and efficacy was evaluated in a modified intent to treat (mITT)

population that received at least 1 dose of study drug and had at least one treatment evaluation. Efficacy was evaluated both as a primary end-point in the modified intent-to-treat (mITT) population and also as a primary end point in a Completers population that included all patients that completed the entire protocols as described above.

Results

Patients who received the 20 µg dose, but not patients receiving the 40 µg dose, showed a sustained improvement in SIB versus baseline as well as the placebo patients throughout the 13-week trial (FIG. 1). It is hypothesized that the lack of efficacy of the higher, 40 µg, dose was due to prolonged down regulation of PKC that typically follows higher and/or longer levels of PKC activation. Nelson et al., *J Biol Chem.;* 2009 284(50):34514-21. As specified in the Statistical Plan that was approved by the FDA for this exploratory trial, all p-values are 1-sided except as otherwise specified, as for example for correlation p-values (see below), post-hoc trend analyses, and post-hoc non-Namenda SIB improvement analyses based on direct serial regressions, which have 2-sided p-values. The results presented include Top Line, initial results, analysis of exploratory endpoints, and analyses of post-hoc endpoint results.

Sensitivity Analyses

Several sensitivity analyses were conducted and validated as described below. MMRM (mixed model for repeat measures) analyses for Completers were largely consistent with the corresponding FAS analyses across several key endpoints, including change-from-baseline scores for SIB Total, ADCS-ADL SEV Total, and NPI. MMRM analyses for MMSE-2 and CGI-I generally showed less separation among treatment groups than was observed for the corresponding MMRM analyses for SIB Total Score. Analysis of Covariance (ANCOVA) and MMRM models for SIB Total Score and ADCS-ADL Total Score were generally similar across various sensitivity analyses. Standard errors for the Treatment Difference across endpoints (Changes Scores for SIB Total, ADCS-ADL Total, MMSE-2, and NPI) and Models (ANCOVA/MMRM with and without Site, including efficacy of acetyl-cholinesterase-inhibitor (AChEI) as a factor, and including only larger sites) were very similar compared to the corresponding standard errors for the treatment differences in the main models.

Several additional sensitivity analyses included a random site term gave results which were very similar to the results for the fixed effects model. This reinforces reliance on the primary model, which reasonably accounts for the effect of dropouts, the impact of sites, and baseline covariates. Using a quantitative baseline MMSE variable resulted in a slight improvement in sensitivity, but the results were very similar to the results using a categorical factor for baseline MMSE stratification. A sensitivity analysis using z-score carried forward (using two iterations) to account for dropouts and increase power was also conducted. The first iteration of the z-score imputation shows some separation of the treatment groups as compared to the original means from the MMRM model. The second iteration of the z-score imputation showed results which were very similar to the results from the first iteration, indicating that two iterations was sufficient. Although there was some improvement in power, the results were similar enough to the results from MMRM that the use of z-score imputation was not needed. Correction for baseline NPI Total Score was done in the primary mixed model to assess the possible impact. Forest plots show better effects for some items, especially for the 40 µg dose. The results across endpoints were much more consistent with each other than the results without the correction for baseline NPI.

Significant SIB Improvement at 5 Weeks was Correlated with Weeks 9 and 13 Efficacy:

By week 5 (after 3 bryostatin doses had been administered), patients in the 20 µg arm showed a significant improvement (FIG. 1) in the SIB scores compared to the placebo patients and compared to their baseline scores ($p=0.016$, Completers' Group; $p=0.056$; FAS).

As shown below (Table 1), the magnitude of the change scores in the 20 µg group at 5 weeks was significantly correlated with the change scores observed at 9 and 13 weeks ($p<0.001$). These and other between-week correlations support the consistency of the SIB improvements produced by the 20 µg doses throughout the trial. These correlations also suggest that the patients who showed improvement at 5 weeks ($p=016$) were the same patients who showed improvement at 9 and 13 weeks. The placebo group showed similar between visit correlations with the strongest correlations between weeks 5, 9, and 13($p<0001$).

The correlations between visits were generally not as strong in the 40 µg group (found to produce no SIB improvement) at any of the visits. The correlations and p-values for the change scores for SIB (and ADC—poor between-group correlations) for the 20 µg group are given in Table 1 below.

TABLE 1

Correlations and p-values for Total SIB and ADCS-ADL Change Scores by Visit for the Bryostatin 20 µg group Table 1:

| Bryostatin 20 µg | | SIB Week 5 | SIB Week 9 | SIB Week 13 | ADL Week 5 | ADL Week 9 | ADL Week 13 |
|---|---|---|---|---|---|---|---|
| SIB Week 5 | Correlation | 1 | 0.54375 | 0.52677 | 0.24549 | 0.11371 | 0.05365 |
|  | p-value |  | 0.0004 | 0.0007 | 0.1126 | 0.5028 | 0.7525 |
| SIB Week 9 | Correlation |  | 1 | 0.77013 | 0.28524 | 0.41538 | 0.34885 |
|  | p-value |  |  | <.0001 | 0.087 | 0.0106 | 0.037 |
| SIB Week 13 | Correlation |  |  | 1 | 0.24172 | 0.2795 | 0.15441 |
|  | p-value |  |  |  | 0.1495 | 0.0988 | 0.3615 |
| ADL Week 5 | Correlation |  |  |  | 1 | 0.75136 | 0.58849 |
|  | p-value |  |  |  |  | <.0001 | 0.0001 |
| ADL Week 9 | Correlation |  |  |  |  | 1 | 0.70214 |
|  | p-value |  |  |  |  |  | <.0001 |
| ADL Week 13 | Correlation |  |  |  |  |  | 1 |

At 30 Days Post-Dosing (Week 15), the 20 µg Group Showed SIB Improvement:

The SIB efficacy measurement at 30 days (week 15) post dosing—after all dosing had been completed (last dose administered at week 11)—was a pre-specified exploratory endpoint. Week 15 results were only included for subjects who were not re-randomized. The mixed model assumes missing at random, but order of enrollment in the trial was not random. Since order of enrollment was not random, the assumption of missing at random is not met. For this reason, only including week 15 for those who were not re-randomized is an appropriate way to estimate week 15 results, but not an appropriate way to estimate results at the earlier visits. For this reason, estimates up through week 13 are from a mixed model that only included data through week 13 and the week 15 estimates are from a separate model. Results were generated using a mixed model with repeated measures predicting change from baseline in SIB Total Score as the response variable and using baseline score, baseline MMSE strata, treatment, visit (categorical), and visit (treatment) as predictors.

Figure 2:
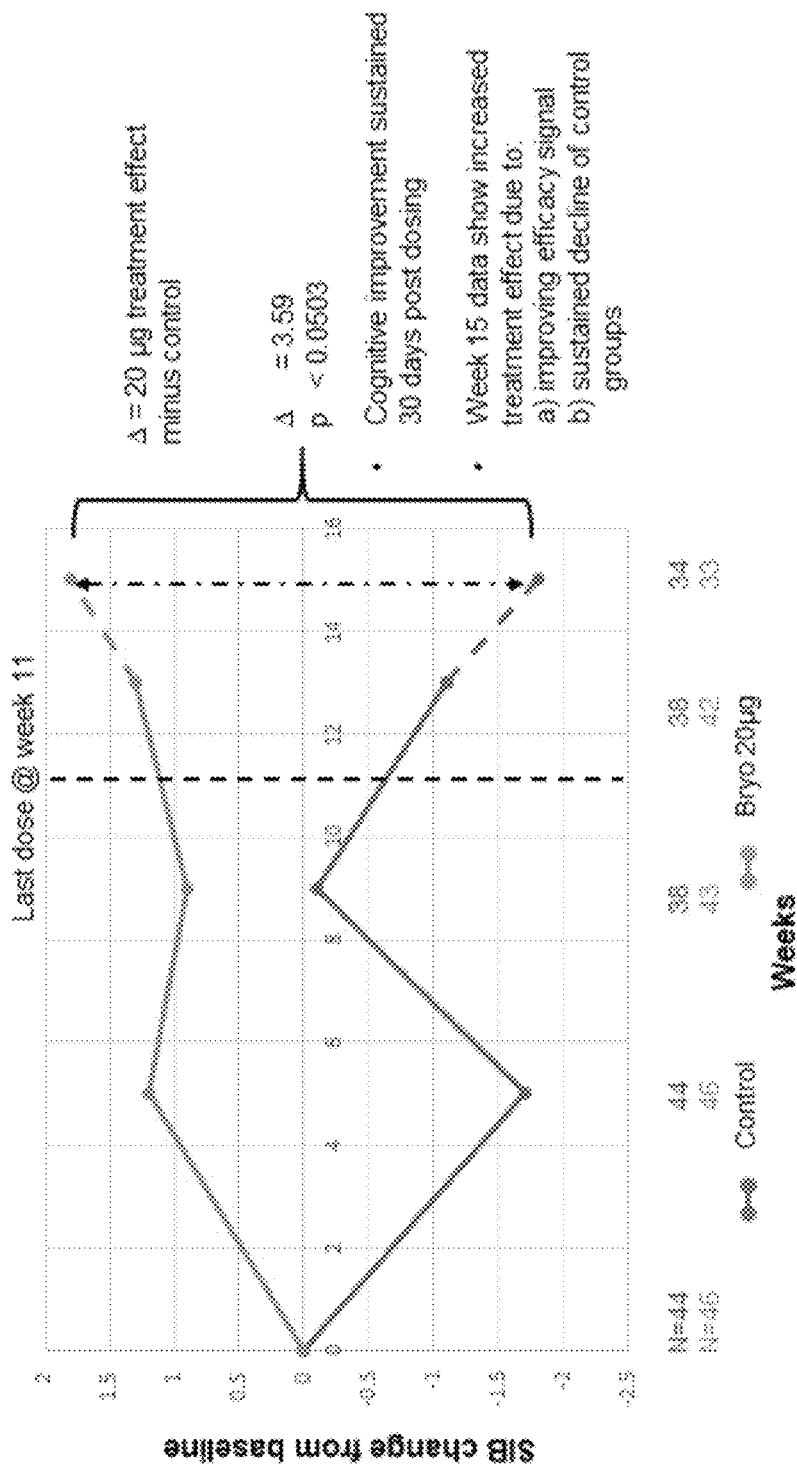
FIG. 2 is a graph showing the SIB change from baseline compared to placebo 30 days post dosing in the mITT population.
Figure 3:
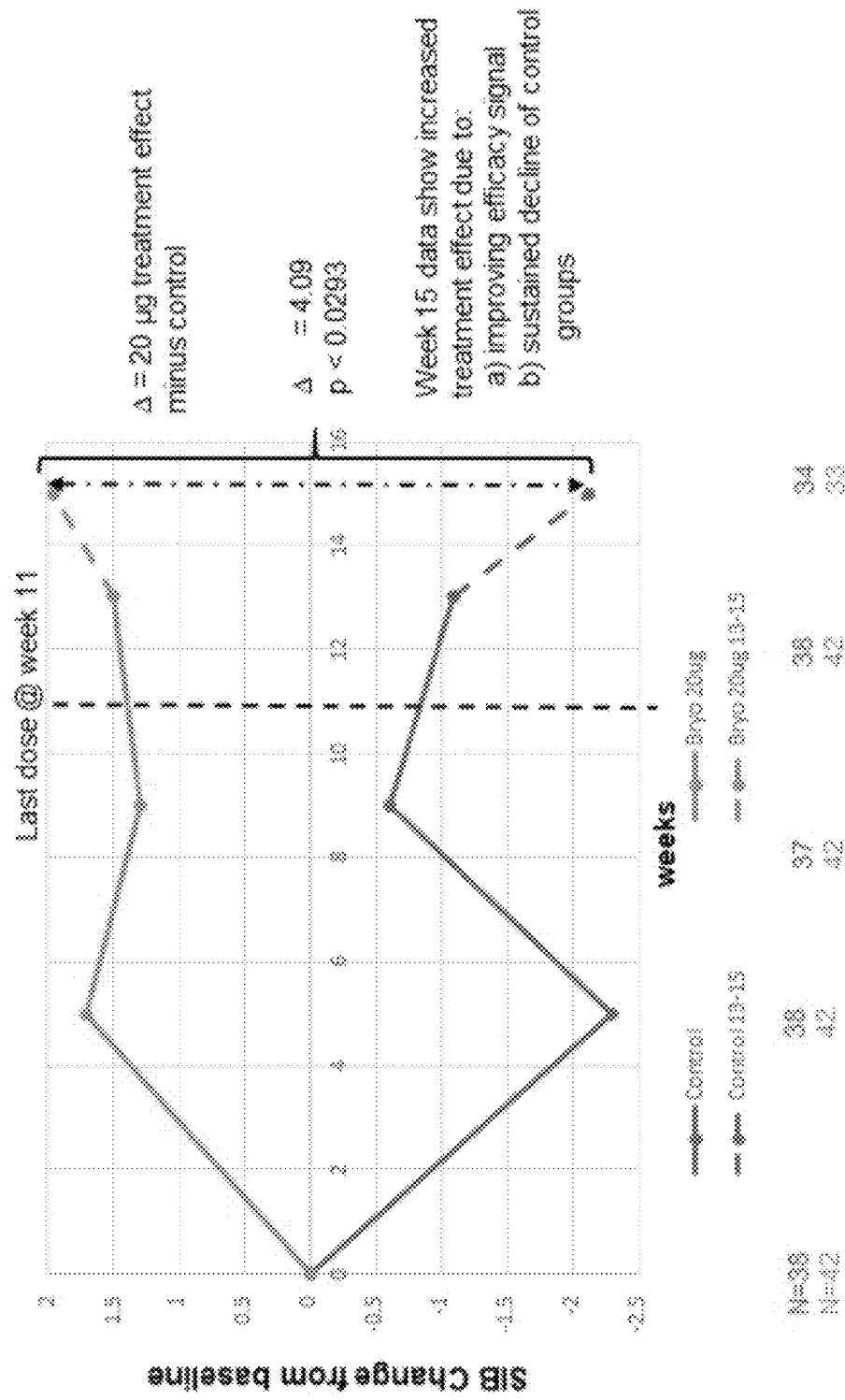
FIG. 3 is a graph showing the SIB change from baseline compared to placebo 30 days post dosing in the Completers population.

The 20 µg patients (including week 15 for all subjects who were not re-randomized—FAS) showed a consistent improvement at week 15 (approximately 30 days after the last scheduled dose of bryostatin at 11 weeks) in their SIB scores over baseline and as compared to the Placebo patients (p=0.0503). In contrast to the 15-week SIB LS Mean improvement of 1.77, the Placebo patients showed a decline in their LS Mean SIB scores of 1.82 (with a treatment difference of 3.59) points from Baseline to week 15 (see Table 2 and FIG. 2). For the Completers group, there was a persistent improvement (30 days after the last scheduled dose of bryostatin at 11 weeks) in their SIB scores over baseline and as compared to the Placebo patients (p=0.0293). This corresponds to a treatment difference of the 20 µg patients from Placebo patients at 15 weeks of 4.09 (See FIGS. 2 and 3).

Dose Efficacy is Supported when Efficacy is Referenced to Body Surface Area Analysis (BSA)

Normalization of the 20 µg doses to each patient's BSA (body surface area) revealed that the 20 µg doses—on a per-patient-basis were tightly distributed around the 12.5 µg/m$^2$ (20 µg) dose, whereas the 40 µg doses on a per-patient-basis were broadly distributed around 25 µg/m$^2$. The week 13 mean dose adjusted for body surface area was 11.33 µg/m$^2$ in the 20 µg dose group and was 21.34 µg/m$^2$ in the 40 µg dose group. These differences in distribution, as quantified by the F ratio (the ratio of the variance measures for 20 µg and the 40 µg dose distributions) suggest that the 20 µg dose patients may have received effective dose levels—at the frequency used in this protocol (cf. AAIC, 2017). The ratio of the variance for the 40 µg group divided by the variance for the 20 µg group results in an F-ratio of 3.97 and a corresponding 2-sided p-value of <0.0001, supporting a conclusion of unequal variances. See FIG. 8. Comprehensive BSA results for both bryostatin dose groups by visit showed that results for completers were similar to those from the mITT population.

Figure 8:
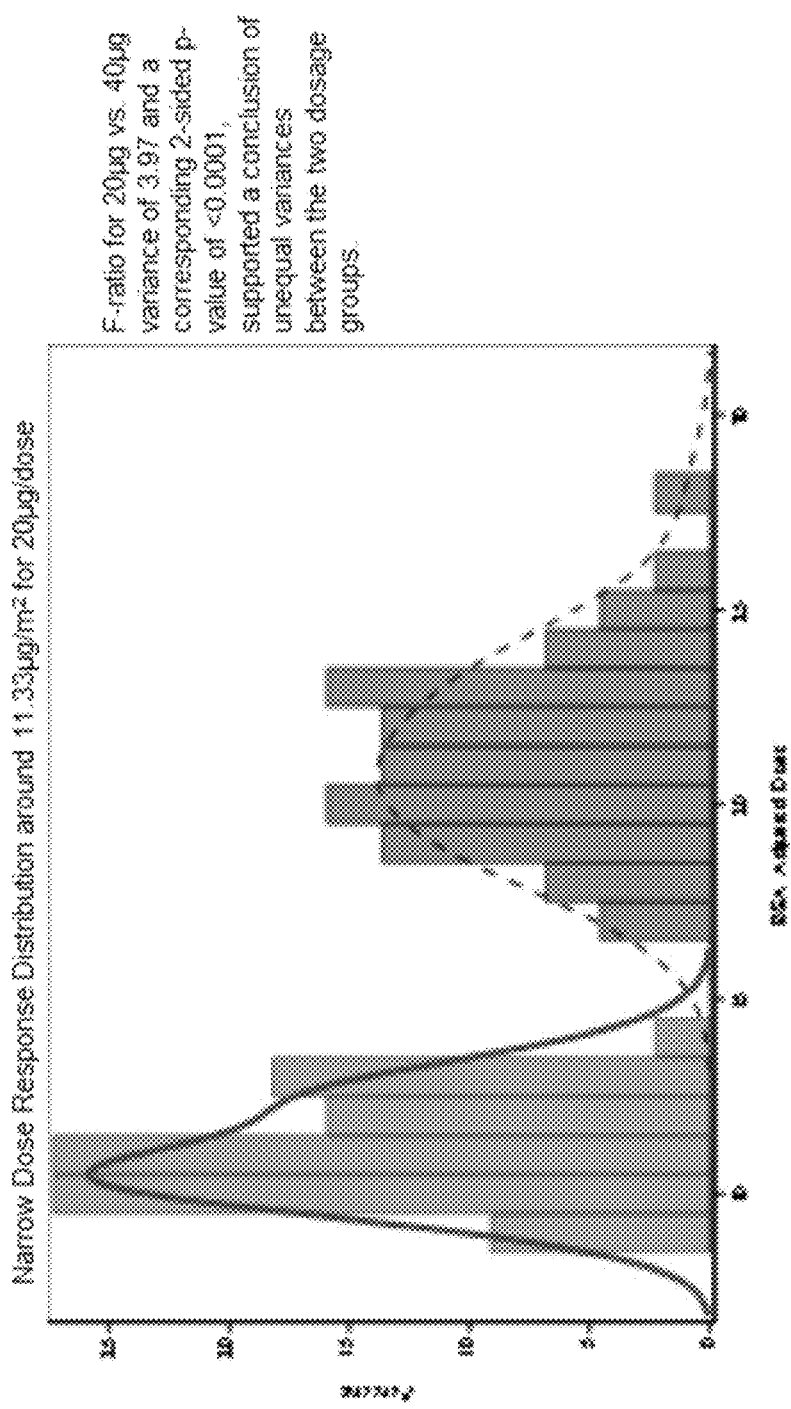
FIG. 8 is a graph showing the Body Surface Area analysis of a bryostatin dose.

FIG. 8 shows the distribution with BSA normalization for both bryostatin dose arms for subjects with SIB Total scores at Week 5. The figures for each additional follow-up visit are similar since the BSA data is unchanged. The only difference between figures is that subjects who were missing SIB Total score at the specified visit were not represented in the figure for that visit.

Memantine Blocks Bryostatin SIB Improvement:

Results were generated using a mixed model with repeated measures predicting change from baseline in SIB Total Score as the response variable and using baseline score, baseline MMSE strata, treatment, visit (categorical), visit*treatment, memantine use*treatment, and memantine use*treatment*visit as predictors. Again, results from week 15 were obtained from a separate model that included week 15 data for subjects who were not re-randomized. Results up

TABLE 2

| By Visit SIB Total: MMRM for Bryostatin 20 µg vs. Placebo | | | | |
|---|---|---|---|---|
| Time Point | | Placebo - FAS | Bryostatin 20 µg - FAS | Placebo - Completer | Bryostatin 2 µg - Completer |
| Week 5 | n | 46 | 44 | 42 | 38 |
| | LS Mean (SE) | -1.77 (1.496) | 1.18 (1.102) | -2.33 (1.583) | 1.67 (0.964) |
| | Difference vs. Placebo | | 2.96 | | 4.00 |
| | p-value | | 0.0563 | | 0.0164 |
| | 80% CI for the difference | | 0.58, 5.34 | | 1.63, 6.38 |
| Week 9 | n | 43 | 38 | 42 | 37 |
| | LS Mean (SE) | -0.09 (1.469) | 0.94 (1.149) | -0.57 (1.539) | 1.28 (1.119) |
| | Difference vs. Placebo | | 1.03 | | 1.85 |
| | p-value | | 0.2898 | | 0.1650 |
| | 80% CI for the difference | | -1.36, 3.42 | | -0.59, 4.29 |
| Week 13 | n | 42 | 38 | 42 | 38 |
| | LS Mean (SE) | -0.79 (1.328) | 1.16 (1.150) | -1.12 (1.387) | 1.51 (1.118) |
| | Difference vs. Placebo | | 1.94 | | 2.63 |
| | p-value | | 0.1340 | | 0.0699 |
| | 80% CI for the difference | | -0.31, 4.19 | | 0.35, 4.91 |
| Week 15* | n | 27 | 26 | 27 | 26 |
| | LS Mean (SE) | -1.82 (1.727) | 1.77 (1.342) | -2.13 (1.758) | 1.96 (1.255) |
| | Difference vs. Placebo | | 3.59 | | 4.09 |
| | p-value | | 0.0503 | | 0.0293 |
| | 80% CI for the difference | | 0.79, 6.39 | | 1.33, 6.85 |

*Results from Week 15 are from a model that included all visits.

through week 13 were from a model that included data up through week 13 for all subjects. A difference in SIB efficacy was found in patients treated with 20 µg bryostatin with or without memantine (Namenda) as background SOC therapy.

and a p-value of 0.0576. This comparison in the completer population had a difference of 6.36 and a p-value of 0.0488. Results for the completer population, therefore, were generally similar to the FAS population.

TABLE 3

By Visit SIB Total: MMRM with Covariate Interactions Including Memantine Use

| Time Point | | FAS | | | | Completer | | | |
|---|---|---|---|---|---|---|---|---|---|
| | | Without Memantine | | With Memantine | | Without Memantine | | With Memantine | |
| | | Placebo | Bryostatin 20 µg | Placebo | Bryostatin 20 µg | Placebo | Bryostatin 20 µg | Placebo | Bryostatin 20 µg |
| | Overall Patient Counts, n (%) | 14 (30.4%) | 17 (38.6%) | 32 (69.6%) | 27 (61.4%) | 13 (31.0%) | 16 (42.1%) | 29 (69.0%) | 22 (57.9%) |
| Week 5 | LS Mean (SE) | −1.74 (2.760) | 2.74 (1.786) | −1.70 (1.807) | 0.26 (1.392) | −2.16 (2.898) | 3.22 (1.454) | −2.33 (1.925) | 0.61 (1.224) |
| | Difference vs. Placebo | | 4.48 | | 1.96 | | 5.38 | | 2.94 |
| | p-value | | 0.0857 | | 0.1973 | | 0.0487 | | 0.1016 |
| | 80% CI for the difference | | 0.29, 8.67 | | −1.00, 4.91 | | 1.24, 9.51 | | −0.02, 5.91 |
| Week 9 | LS Mean (SE) | 0.87 (2.714) | 2.95 (1.804) | −0.42 (1.773) | −0.33 (1.444) | 0.69 (2.810) | 3.34 (1.695) | −1.06 (1.866) | −0.16 (1.410) |
| | Difference vs. Placebo | | 2.08 | | 0.09 | | 2.66 | | 0.90 |
| | p-value | | 0.2597 | | 0.4847 | | 0.2071 | | 0.3522 |
| | 80% CI for the difference | | −2.08, 6.23 | | −2.87, 3.05 | | −1.53, 6.84 | | −2.14, 3.93 |
| Week 13 | LS Mean (SE) | −1.29 (2.449) | 3.83 (1.733) | −0.46 (1.608) | −0.60 (1.425) | −1.32 (2.546) | 4.22 (1.639) | −0.96 (1.688) | −0.39 (1.384) |
| | Difference vs. Placebo | | 5.11 | | −0.14 | | 5.53 | | 0.56 |
| | p-value | | 0.0437 | | 0.4752 | | 0.0338 | | 0.3988 |
| | 80% CI for the difference | | 1.30, 8.93 | | −2.92, 2.65 | | 1.68, 9.38 | | −2.27, 3.40 |
| Week 15* | LS Mean (SE) | −0.05 (3.151) | 5.88 (2.036) | −1.61 (2.304) | −0.83 (1.703) | −0.12 (3.225) | 6.24 (2.046) | −2.16 (2.367) | −0.71 (1.728) |
| | Difference vs. Placebo | | 5.93 | | 0.79 | | 6.36 | | 1.45 |
| | p-value | | 0.0576 | | 0.3927 | | 0.0488 | | 0.3120 |
| | 80% CI for the difference | | 1.12, 10.73 | | −2.93, 4.50 | | 1.47, 11.25 | | −2.36, 5.25 |

Figure 4:
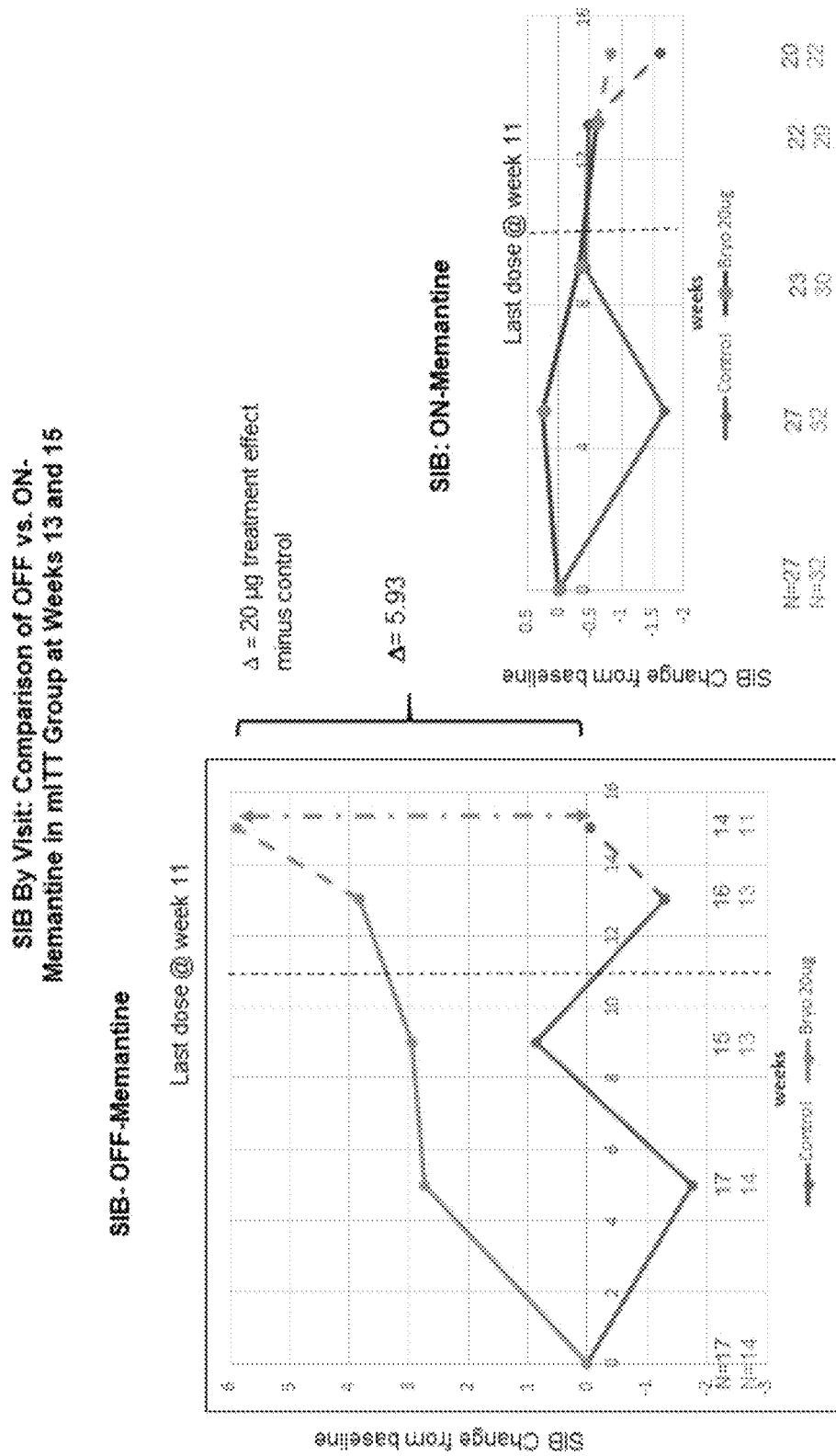
FIG. 4 includes graphs showing the SIB change from baseline compared to placebo for the mITT population treated with bryostatin with or without memantine.
Figure 5:
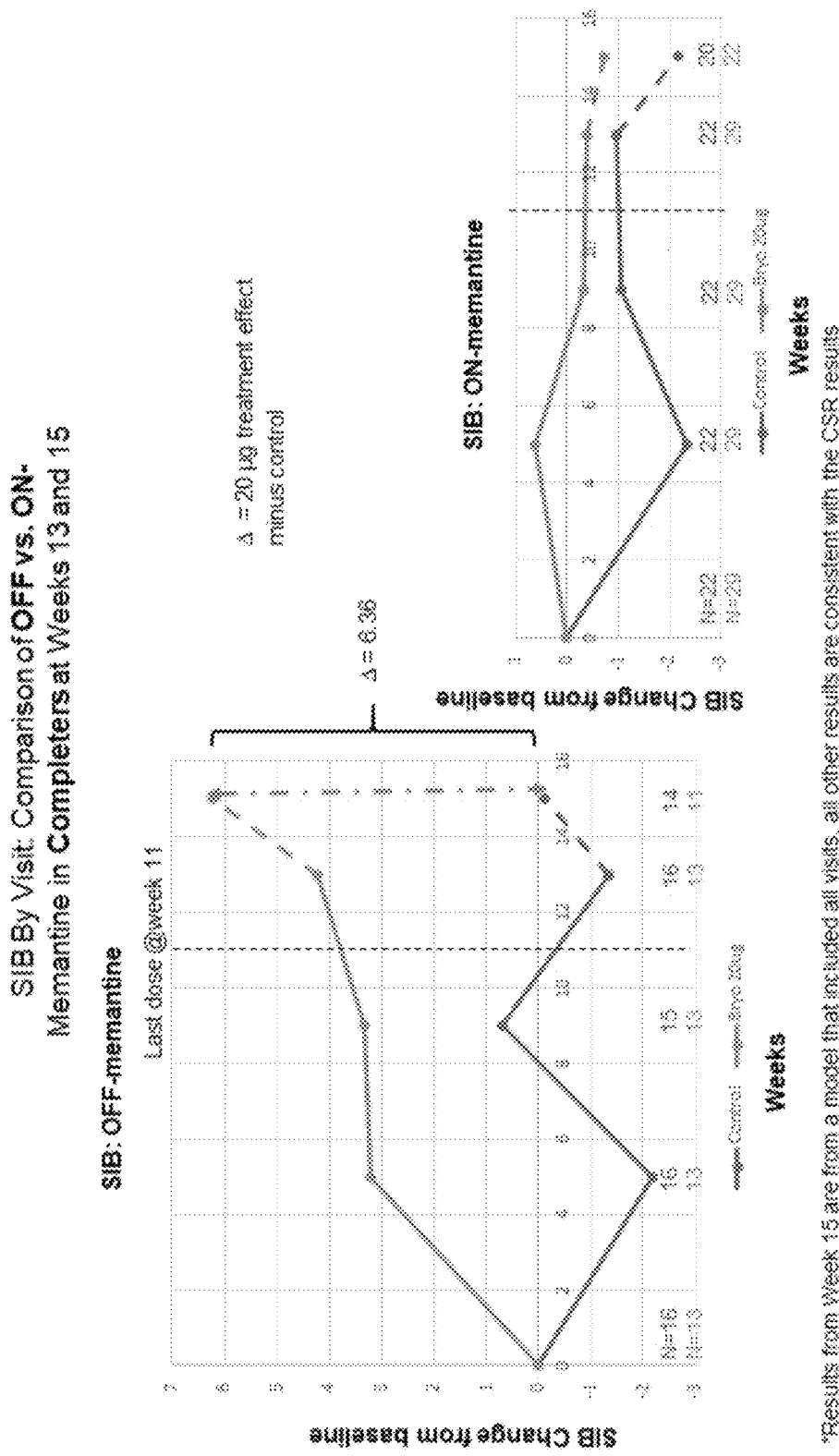
FIG. 5 includes graphs showing the SIB change from baseline compared to placebo for the Completers population treated with bryostatin with or without memantine.

The 20 µg patients (mITT) who were on memantine, a partial NMDA receptor antagonist, showed no improvement in their SIB scores throughout the week 13 observation period when compared to placebo patients (20 µg LS Mean change=−0.60 versus −0.46 for placebo, p=0.4752 for difference). In contrast, the 20 µg without memantine showed improvement throughout the week 13 observation period that was greater than the SIB improvement previously reported (AAIC, 2017) for the entire 20 µg group (see Table 3 and FIG. 4 below). The 13-week LS Mean change in the 20 µg group without memantine was 3.83 points compared to the placebo group LS Mean change of −1.29, with a difference of 5.11 and a p-value of 0.0437. For the Completers patient group, the 13-week LS Mean change in the 20 µg group without memantine showed no improvement in their SIB scores throughout the 13 week observation period when compared to placebo patients (20 µg LS Mean change=0.56 for placebo, p=0.3988 for difference). In contrast, without memantine, the 13-week LS Mean change in the 20 µg (Completers) was 4.22 compared to the Placebo group LS Mean change of −1.32 with a difference of 5.53 and a p-value of 0.0338.

The 15-week LS Mean change in the 20 µg group (mITT) without memantine was 5.88 points compared to the placebo group LS Mean change of −0.05, with a difference of 5.93

As described above, overall, the 15-week LS Mean change for the 20 µg group was 1.77 points, compared to the placebo group LS Mean change of −1.82 points with a difference of 3.59 (p=0.0503). Memantine partially blocks the NMDA glutamate post-synaptic receptor that is well-known to be regulated by PKC phosphorylation. This regulation may explain prevention of bryostatin's therapeutic efficacy for the patients on maintenance doses of Memantine throughout this trial.

Efficacy of Secondary Psychometric, ADCS-ADL

Figure 6:
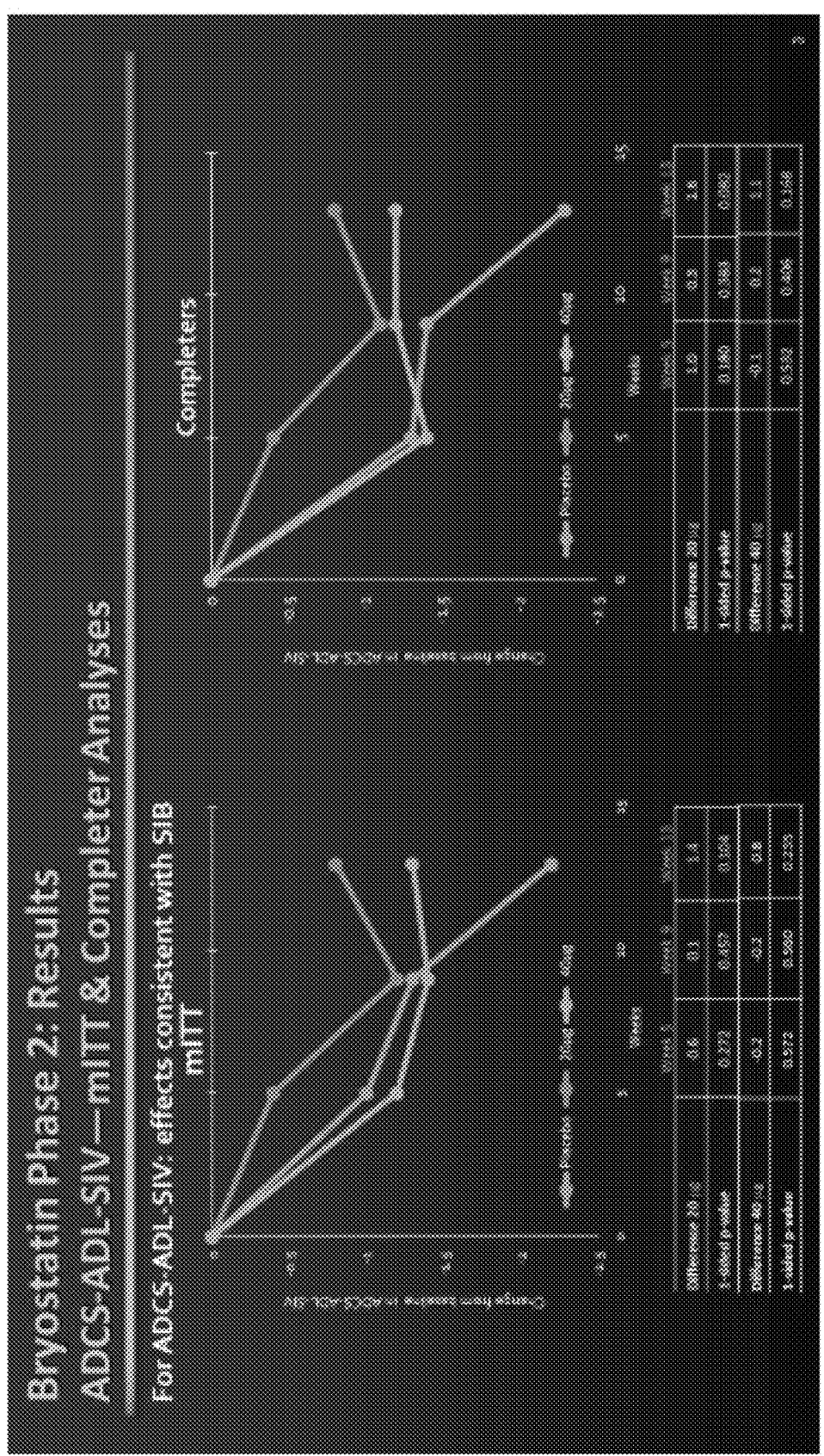
FIG. 6 includes graphs showing the ADCS-ADL-SIV efficacy in the mITT population and the Completers population.
Figure 7:
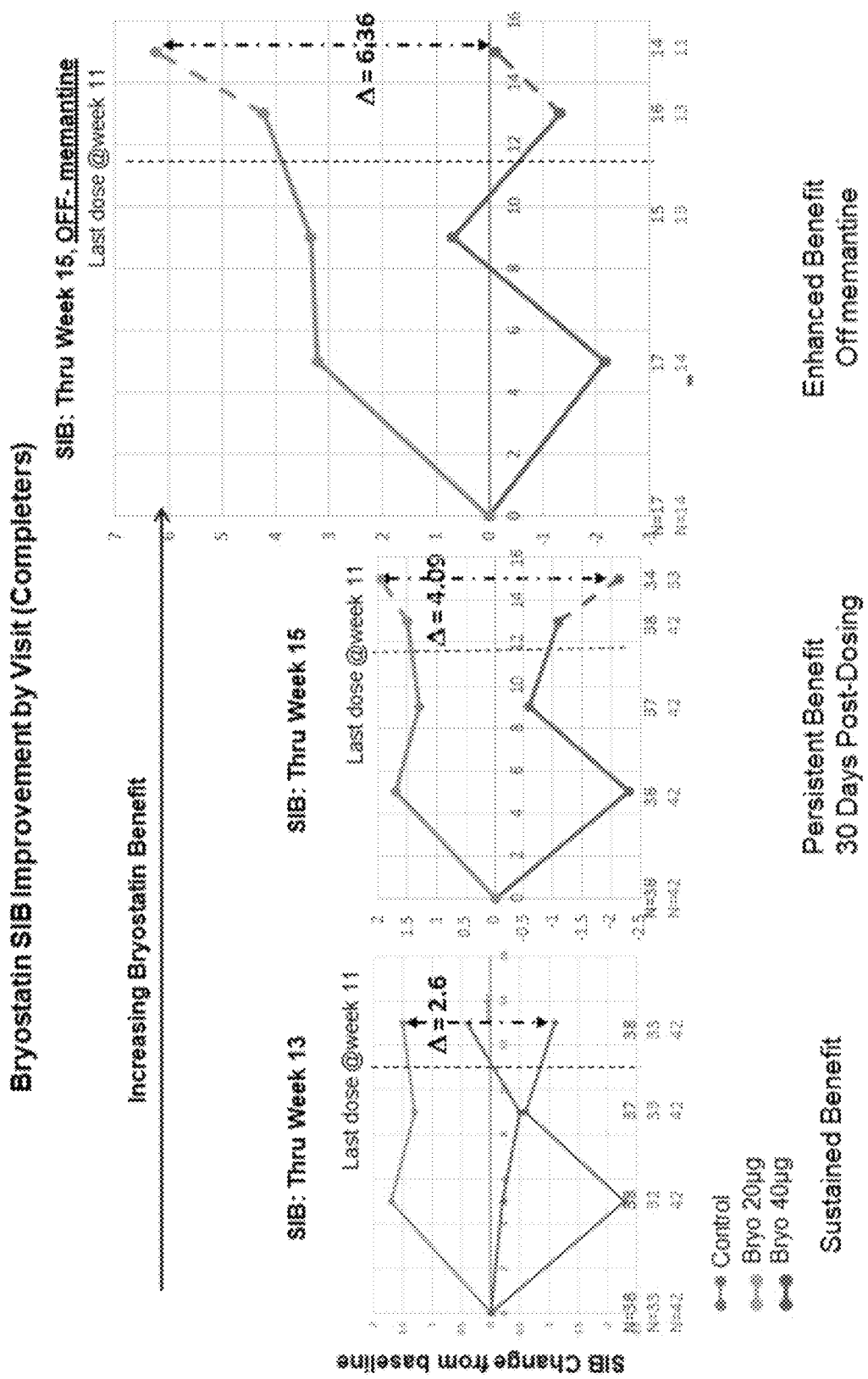
FIG. 7 includes graphs showing the sustained improvement of the SIB versus baseline and placebo 30 days post dosing in the Completers population.

As for the SIB, the ADCS-ADL efficacy was significant for the 20 µg but not the 40 µg dose (FIG. 6). For the 20 µg dose, the mITT group showed a difference from placebo of 1.4 (p<0.104), while for the completers group (20 µg) showed a difference from placebo of 1.6 (p<0.082). Subgroups with and without memantine (Namenda)—as background SOC therapy—were not significantly different above placebo.

There was no evidence of treatment by efficacy of acetylcholinesterase-inhibitor (AChEI) use interaction. For SIB Total, the two sided p-value for the interaction between treatment and AChEI use was 0.8244 and the two sided p-value for the interaction between treatment, AChEI use and time was 0.9223. Similar results were seen when investigating the effect of AChEI use on treatment effect for ADCS-ADL with p-values of 0.5137 and 0.6256 (two sided), respectively. At week 13, the LS Mean difference between 20 µg group and placebo in SIB Total for AChEI non-users was 2.00 and users was 2.09, and in ADCS-ADL for AChEI non-users was −0.67 and users was 1.99.

Sustained SIB Benefit Reinforced by Combined Analyses (A) MMRM-A combined treatment effect across Weeks 5, 9, and 13 was calculated as a summary of the overall treatment effect. The estimated coefficients from the MMRM were used to compute and average three deltas:

Combined=(Δ Week 5+Δ Week 9+Δ Week 13)/3

The difference in the combined average treatment effects between 20 µg and placebo groups was estimated and tested for significance using Least Square Means. For the combined analyses at week 13, the bryostatin 20 µg group in the FAS with the post-hoc MMRM analysis showed the following:

The combined treatment effect from Weeks 5, 9, and 13 showed a mean improvement in SIB of 2.146 (1-sided p=0.093) for bryostatin 20 µg over placebo in the FAS population, and a mean improvement of 3.089(1-sided p=0.032) over placebo in the Completer population.

Using the post-hoc combined analysis method, results for both FAS and completer populations show numerically greater improvement of bryostatin 20 µg over placebo, and reached statistical significance based on the protocol pre-specified 1-sided α=0.10 level.

By showing the summary statistic for the entire treatment period, rather than at an arbitrary specific time point, the results offer a more clinically relevant interpretation—particularly the sustained nature of the SIB improvement caused the cumulative treatment benefits of bryostatin 20 µg.

An additional supplemental post-hoc analysis was conducted using the following SAP-defined exploratory endpoint: Change from baseline in SIB Score at the 30-day follow-up (Week 15 visit). The post-hoc MMRM analysis was performed on the population of patients who have a 30-Day Follow-Up Visit (N=26 for bryostatin 20 µg, and N=27 for placebo for the 17-Week Completer Set) Using the post-hoc analysis method on the 30-Day Follow-up population of patients yields the following:

The combined treatment effect from Weeks 5, 9, 13, and 15 shows a mean improvement in SIB of 4.721 (1-sided p=0.032) for bryostatin 20 µg over placebo. This magnitude of improvement in SIB change is substantially larger than the improvements seen in all previous analyses.

The estimated improvement of bryostatin 20 µg over placebo is greater at each week and for the entire treatment period for this population, and reached statistical significance based on the protocol pre-specified 1-sided α=0.10 level at each visit.

These supplemental analyses of the change in baseline SIB Score at the 30-day follow-up exploratory endpoint further suggests that the treatment benefits of bryostatin 20 µg persist after the treatment period ends.

(B) Simple Comparisons—Post-hoc analyses of SIB scores, for the placebo and low dose bryostatin (20 µg dose) treatment arms, stratified by exposure to memantine.

A total of 57 patients with exposure to memantine (31 placebos and 26 low dose bryostatin patients) and 33 memantine treatment-naïve patients (15 placebos and 18 low dose bryostatin patients) were considered in the post-hoc analyses. Patients used here are from the modified ITT FAS sample (e.g. patients with at least one post-baseline SIB).

Unadjusted Analysis of the Primary Efficacy Endpoint: The primary efficacy endpoint for each individual patient is the change in average of the SIB scores obtained in the 13 to 15-week time window from the baseline SIB score. If a patient is missing from the study at either the 13 week or 15-week time point, then the SIB for this time window is given as the one SIB value obtained. Since the number of patient missing at both the 13 week and 15-week time point was low, no SIB values were imputed. A total of 7 memantine patients and 3 memantine naïve patients in the FAS sample were missing from the study at both week 13 and week 15.

The group difference was statistically assessed by considering the mean primary efficacy endpoint averaged over all patients with endpoint data in each treatment arm. The t-test for two independent samples, assuming unequal variance, was performed on the group difference of these means. In addition, the Wilcoxon rank sum test was also performed to determine the robustness of the t-test.

Tables 4 and 5 below show the treatment arm means (SD) of the primary efficacy endpoint, and the corresponding two-sided p-values from both the test and Wilcoxon tests. Statistical comparisons between treatment differences in the means of the difference in baseline SIB and SIB at times 3, 9, and 13 weeks are given for comparison purposes.

TABLE 4

Simple Comparison of the Primary Efficacy Endpoint by T-test and Wilcoxon Test for the Memantine Treatment-Naïve Patients.

| SIB | Placebo | | Low dose (20) | | T-test | | Wilcoxon test | |
| --- | --- | --- | --- | --- | --- | --- | --- | --- |
|  | Mean | SD | Mean | SD | T | P-val | W | P-val |
| Delta at Week 5 | −1.200 | 10.262 | 3.444 | 5.752 | 1.560 | 0.134 | 88 | 0.091 |
| Delta at Week 9 | 0.786 | 7.444 | 3.467 | 7.039 | 0.995 | 0.329 | 76 | 0.203 |
| Delta at Week 13 | −1.143 | 6.893 | 4.500 | 7.014 | 2.219 | 0.035 | 66 | 0.058 |
| Delta at Ave of Week 13 and 15 | −0.679 | 6.707 | 5.406 | 5.432 | 2.706 | 0.012 |  | 0.016 |

TABLE 5

Simple Comparison of the Primary Efficacy Endpoint by T-test
and Wilcoxon Test for the Memantine Exposed Patients.

|  | Placebo | | Low dose (20) | | T-test | | Wilcoxon test | |
| --- | --- | --- | --- | --- | --- | --- | --- | --- |
| SIB | Mean | SD | Mean | SD | T | P-val | W | P-val |
| Delta at Week 5 | −1.258 | 10.498 | 0.077 | 8.109 | 0.541 | 0.590 | 385 | 0.779 |
| Delta at Week 9 | −0.414 | 11.008 | −0.087 | 6.522 | 0.133 | 0.895 | 328 | 0.919 |
| Delta at Week 13 | −0.464 | 10.031 | −0.545 | 6.508 | −0.035 | 0.973 | 318 | 0.852 |
| Delta at Ave of Week 13 and 15 | −1.768 | 10.306 | −0.727 | 6.388 | 0.438 | 0.664 |  | 1.000 |

Adjusted Analysis of the Primary Efficacy Endpoint: Because the post-hoc analyses presented here focuses on the subgroup of patients defined by memantine exposure, there can be no assumption that randomization controlled for the potential imbalance of baseline factors between the placebo and bryostatin treatment arms within the memantine exposure strata. Thus, any possible difference between treatment arms within the memantine strata could be confounded by memantine exposure. For example, it is possible that bryostatin-treated patients in the memantine treatment-naïve group are more likely to be in the higher MMSE-2 strata versus memantine treatment-naïve placebo, which in turn might result in a higher SIB endpoint for these patients.

Analyses of Covariance models were created to control for potential baseline imbalances. These models compare differences in the group means of the primary efficacy endpoints (SIB at 13/15 weeks from baseline) with the memantine strata, while controlling for the SIB at baseline and the MMSE-2 strata at randomization. Table 6 shows the regression results for both memantine naïve and memantine exposed groups.

TABLE 6

Baseline SIB and MMSE-adjusted Slopes for Placebos
and 20 μg Bryostatin Patients by Memantine exposure.

|  | Memantine Naïve | | Memantine Exposed | |
| --- | --- | --- | --- | --- |
|  | Baseline SIB | Base SIB, MMSE- 2 | Baseline SIB | Base SIB, MMSE- 2 |
| Treatment (95% CI) | 5.426 (p = 0.010) (1.402, 9.451) | 5.923 (p = 0.002) (2.328, 9.518) | −0.531 (p = 0.843) (−5.877, 4.816) | −0.620 (p = 0.815) (−5.925, 4.685) |
| Baseline SIB (95% CI) | −0.180 (p = 0.005) (−0.302, −0.058) | −0.243 (p < 0.001) (−0.361, −0.126) | 0.131 (p = 0.116) (−0.034, 0.295) | 0.048 (0.636) (−0.155, 0.252) |
| MMSE-2 (95% CI) |  | 6.790 (p = 0.008) (1.942, 11.638) |  | 4.266 (p = 0.183) (−2.081, 10.613) |

Analysis of Linear Trends in SIB over Time: In addition to considering the difference in treatment means of the change of SIB at each time point from the baseline, the change in SIB values over all the time points was also considered. Initially, the slope of each person's trajectory over all time points was estimated, from baseline (week 0) to the week 15. The mean slopes were then calculated for treatment arm within both memantine strata. The means of the treatment-specific slopes were statistically compared using the two-sample t-test and Wilcoxon rank sum test.

Table 7 shows the mean (95% CI) of the slope for each treatment and memantine exposure combination for the unweighted data as well as these data weighted by the number of non-zero SIB measures.

TABLE 7

Mean (95% CI) Slopes, both Unweighted and Weighted by the Number of Non-Zero SIB scores.

|  | Placebo | 20 μg Bryostatin | t-test Wilcoxon | Placebo | 20 μg Bryostatin | t-test Wilcoxon |
| --- | --- | --- | --- | --- | --- | --- |
| Unweight Slope | 0.152 (−0.124, 0.428) | 0.382 (0.130, 0.634) | P = 0.210 P = 0.047 | −0.002 (−0.391, 0.387) | −0.143 (−0.568, 0.282) | P = 0.627 P = 0.911 |
| Weighted Slope | 0.067 (−0.166, 0.300) | 0.363 (0.146, 0.581) | P = 0.067 | −0.050 (−0.355, 0.254) | −0.099 (−0.437, 0.238) | P = 0.831 |

Discussion:

The effects described above suggest that the 20 μg dose of bryostatin can safely produce sustained improvements in SIB scores of moderate to severe AD patients measured at week 13, and that these improvements may be sustained for weeks (e.g., week 15) after the termination of the dosing protocol (week 11). Bryostatin produces enhanced SIB improvement in the absence of memantine, as shown in FIGS. 1-7 and Table 3 above. Patients on memantine showed no SIB improvement at week 13 or 15 (See FIGS. 4, 5). Collectively, the overall weight and consistency of the data provide a basis for a cognitive-improvement efficacy of bryostatin for the advanced AD patient.

These results, of an exploratory trial of bryostatin in the treatment of advanced Alzheimer's disease patients, are worth considering in the context of all prior drug trials for the treatment of advanced Alzheimer's patients.

Previous trials, ranging from neurotransmitter agonists and/or antagonists to anti-amyloid antibodies and to gamma secretase inhibitors, have rarely if ever produced sustained benefit (vs. placebo) in advanced AD patients.

Here, in every analysis that was conducted, unadjusted, adjusted with MMRM, for 13 weeks and for 15 weeks (30 days post completion of all drug dosing) showed sustained improvement of the SIB vs. baseline and placebo group patients. At 13 weeks for the Completers, the delta improvement was 2.6; at 15 weeks, the improvement delta was 4.0; and at 15 weeks—in the absence of memantine—the delta was 6.36 (See FIG. 7). According to the pre-specified statistical plan, all of these delta values were significant.

In contrast to this observed improvement of SIB, most, if not all, trials directed toward disease modification, have had a different improvement objective: a reduction in the rate of decline of SIB (vs. a shift of decline to improvement). None of these trials has yet succeeded.

The sustained improvement demonstrated with bryostatin began at 5 weeks in the Completers' group (p<0.016) that was correlated with high statistical significance (p<0.001) with improvement at 9, 13, and 15 weeks. These correlations suggest that the same patients benefited throughout the 15-week trial.

It is also worth emphasizing that the memantine blocked all benefit of bryostatin in the SIB improvement. The principle targets of bryostatin, PKC isozymes, are known to regulate NMDA receptor functions (blocked by memantine). Therefore, blockade of the NMDA receptor could offset most if not all of the bryostatin-induced SIB improvement. PKC regulation of the NMDA receptor functions includes increasing NMDA conductance by relieving Mg++ blockade, controlling trafficking of the NMDA receptor to the neuronal membranes, and enhancing NMDA-induced synaptogenesis. This synaptogenesis, a primary mechanism of action (MOA) of bryostatin demonstrated in a variety of pre-clinical models, is mediated by bryostatin-PKC epsilon enhancement of several synaptic growth factors that include BDNF, NGF, and IGF.

The apparent bryostatin-induced persistence of SIB improvement is consistent with a long-lasting consequence of PKC epsilon-growth factor efficacy that could induce the growth and/or maturation of synaptic networks in the brain. The present example describes the first multiple bryostatin dose treatment of AD patients in a double-blind, randomized, placebo-controlled phase 2 trial for 12 weeks. The results described herein surprisingly and unexpectedly suggest that a dose level of 20 mcg can safely produce sustained improvements in the Severe Impairment Battery (SIB) scores of moderate to severe AD patients measured at week 13. Moreover, these improvements may be sustained up to 4 weeks after the termination of the dosing protocol at 11 weeks. This efficacy was only apparent in the absence of baseline, standard of care memantine therapy.

Example 2

The following prophetic example provides a further assessment of the safety, tolerability and efficacy of bryostatin in the treatment of moderately severe to severe Alzheimer's disease subjects not receiving memantine treatment. This randomized double-blind placebo-controlled, confirmatory study will compare bryostatin to placebo for the treatment of moderately severe to severe Alzheimer's disease in subjects not receiving memantine treatment. The study may be 15 weeks in duration, including a safety and efficacy evaluation 30 days after the last dose of study drug. Subjects will receive 7 doses of drug during the study. The primary efficacy endpoint will be the Severe Impairment Battery (SIB) scale score after 12 weeks of treatment (e.g., taking an average of SIB measures observed during the Week 13 to Week 15 time window). Bryostatin-1 or matching Placebo will be administered intravenous by continuous infusion over 45±5 minutes.

Eligible subjects will be stratified based on Mini Mental State Exam (MMSE-2) scores 4-9 vs. 10-15 and will be randomized 1:1 to one of two treatment arms: 20 μg bryostatin or placebo for twelve weeks. The first two doses of study drug will be a loading dose 20% higher (i.e., 24 μg) than the assigned dose and will be administered one week apart. Thereafter, the assigned dose of 20 μg will commence with the third dose and be administered every other week. Drug is administered IV by continuous infusion over 45(±5) minutes. Subjects are scheduled to receive seven doses over 12 weeks. Subjects who drop out prior to completing the Week 7 visit will be replaced, up to a maximum of 15 subjects. Safety and tolerability may be determined through evaluations of adverse events (AE), serious adverse events (SAE), physical examination (PE), vital signs, 12-lead electrocardiogram (ECG), the Columbia Suicide Severity Rating Scale (C-SSRS), and clinical laboratory assessments.

Cognitive improvements will be evaluated primarily with the Severe Impairment Battery (SIB) and secondarily with functional improvements in the Alzheimer's Disease Cooperative Study-Activities of Daily Living-Severe Impairment Version (ADCL-ADL-SIV), Clinical Global Impression of Improvement (CGI-1), and Neuropsychiatric Inventory (NPI) metrics. The primary efficacy endpoint is defined as the SIB scale score obtained between 13 and 15 weeks post first dose. The average SIB score at 13 and 15 weeks will be the primary efficacy end point for patients with SIB outcome measures at both time points; otherwise, either the 13-week or 15-week SIB will be considered as the primary efficacy endpoint for patients present in the study at only one of these two times. The primary efficacy analysis is based on the two-sample t-statistics of the treatment group averages from the primary endpoint. A Wilcoxon test will also be performed.

Patients treated with bryostatin may experience a greater improvement in cognitive function as measured by the SIB from baseline to the primary efficacy endpoint after 12 weeks of treatment, as compared to patients on placebo during the same time period. The null hypothesis will be rejected at a significance level of a two-sided $\alpha=0.05$. The test of the null hypothesis will be a superiority test based on the two-sample t-test, and only an improvement in the SIB score from baseline is of clinical significance.

One of skill in the art will appreciate that the examples herein are not intended to be limiting and that one of skill in the art will readily be able to apply the teachings herein to treating Alzheimer's disease. Therefore, the present methods and compositions are well adapted to attain the ends and advantages mentioned as well as those that are inherent therein. While numerous changes may be made by those skilled in the art, such changes are encompassed within the spirit of this disclosure as illustrated, in part, by the appended claims.

What is claimed is:

1. A method for inducing synaptogenesis in a subject having synaptic loss, the method comprising intravenously administering to the subject a therapeutically effective amount of a synaptic growth factor activating compound to result in an increase in synaptogenesis in said subject, wherein the synaptic growth factor activating compound is administered for the first two doses at about 24 micrograms followed by four consecutive doses of about 20 micrograms each.

2. The method of claim 1, wherein the synaptic growth factor is selected from the group consisting of brain-derived neurotrophic factor (BDNF), nerve growth factor (NGF), and insulin-like growth factor (IGF).

3. The method of claim 1, wherein the method increases BDNF levels.

4. The method of claim 1, wherein the method prevents cognitive loss.

5. The method of claim 1, wherein the method restores lost synapses.

6. The method of claim 1, wherein the synaptic growth factor activating compound is combined with a non-growth factor PKC activator, wherein PKC is protein kinase C.

7. The method of claim 1, wherein the subject is not administered an N-methyl-D-aspartate (NMDA) receptor antagonist.

8. The method of claim 1, wherein said four consecutive doses are administered every other week.

9. The method of claim 1, wherein said first two doses at about 24 micrograms are followed by at least four consecutive doses of about 20 micrograms each.

10. A method for inducing synaptogenesis in a subject having synaptic loss, the method comprising intravenously administering to the subject a therapeutically effective amount of a protein kinase C (PKC) activator to result in an increase in synaptogenesis in said subject, wherein the PKC activator is administered for the first two doses at about 24 micrograms followed by four consecutive doses of about 20 micrograms each.

11. The method of claim 10, wherein said PKC activator is a PKC-ε or PKC-α activator.

12. The method of claim 10, wherein said PKC activator is non-toxic.

13. The method of claim 10, wherein the method increases brain-derived neurotrophic factor (BDNF) levels.

14. The method of claim 10, wherein the method prevents cognitive loss.

15. The method of claim 10, wherein the method restores lost synapses.

16. The method of claim 10, wherein the subject is not administered an N-methyl-D-aspartate (NMDA) receptor antagonist.

17. The method of claim 10, wherein the PKC activator functions to enhance activity of a growth factor.

18. The method of claim 17, wherein the growth factor is selected from the group consisting of brain-derived neurotrophic factor (BDNF), nerve growth factor (NGF), and insulin-like growth factor (IGF).

* * * * *